United States Patent [19]

Wajszczuk et al.

[11] 4,448,202
[45] May 15, 1984

[54] BIOLOGICAL SIGNAL AMPLIFIER SYSTEM WITH NOISE LEVEL REDUCTION

[76] Inventors: Waldemar J. Wajszczuk, 4489 Patrick, West Bloomfield, Mich. 48033; Tadeusz Palko, Gorlicka, 15 A m 10; Grzegorz Pawlicki, Prosta 2/6, both of Warsaw, Poland

[21] Appl. No.: 371,710
[22] Filed: Apr. 26, 1982
[51] Int. Cl.³ .............................................. A61B 5/04
[52] U.S. Cl. .................................................... 128/709
[58] Field of Search ............... 128/695, 696, 706, 901, 128/902

[56] References Cited

U.S. PATENT DOCUMENTS

| | | | |
|---|---|---|---|
| 3,123,768 | 3/1964 | Burch et al. | 128/710 |
| 3,757,778 | 9/1973 | Graham | 128/902 |
| 3,868,948 | 3/1975 | Gragtz | 128/902 |
| 3,871,363 | 3/1975 | Day | 128/697 |

Primary Examiner—William E. Kamm
Attorney, Agent, or Firm—Reising, Ethington, Barnard, Perry & Milton

[57] ABSTRACT

A biological amplifier system is disclosed for displaying the cardiac conduction system activity, particularly the His bundle activity on a beat-to-beat basis by a non-invasive technique. Plural sets of bipolar leads are connected by electrodes to the body surface so as to obtain the same biological signal on each set. The leads are connected in parallel to plural low noise amplifiers which provide simultaneous but separate amplification of the same signal. The amplified signals are added together in a summing circuit with the effect of noise reduction by averaging the random noise components. Noise reduction is further enhanced by use of negative feedback to a reference electrode and by use of a low pass filter and notch filter.

7 Claims, 7 Drawing Figures

BIOLOGICAL SIGNAL AMPLIFIER SYSTEM WITH NOISE LEVEL REDUCTION

FIELD OF THE INVENTION

This invention relates to medical instrumentation and more particularly it relates to an improved low noise amplifier system for biological signals.

BACKGROUND OF THE INVENTION

For diagnostic and other purposes, it is desired to display certain low level electrical signals originating in the body which are of such low potential that they cannot be displayed with conventional instrumentation. A particular field of concern is the study of the cardiac conduction system activity.

An important part of the clinical evaluation of the function of the cardiac conduction system is a method, introduced by Scherlag, for studying the His bundle activity. This method is described by Scherlag in Circulation Vol. 39, page 13, 1969. The Scherlag method was carried out during right heart catheterization and, because of its invasiveness, its application has been limited. Accordingly, a non-invasive technique for detection of the cardiac conduction system activity (from the body surface) is needed.

The His bundle activation voltage has a low level of transmission to the chest wall, typically below 10 microvolts and most commonly about 2 to 5 microvolts. At this low level, it cannot be detected and displayed with conventional electrocardiographic techniques which utilize relatively low gain amplification. Higher amplification in otherwise conventional electrocardiographs result in the signal being obscured by noise originating in the amplifiers, ambient electrical fields, musculoskeletal activity and electrode-skin interface. Such noise components have random characteristics and can be eliminated by signal averaging and filtering. Systems have been developed with improved signal-to-noise ratio by averaging several consecutive cardiac cycles for detection of the electrical activity occurring between the end of the P wave (atrial activity) and the QRS complex (ventricular activity). This signal averaging technique has the shortcoming that it cannot be used for evaluation of individual cardiac cycles. Thus, it is not useful for a study of multifocal arrhythmias or transient events such as intermittent conduction delays or blocks.

A general object of this invention is to provide apparatus for displaying the activity of the cardiac conduction system from a single cardiac cycle on a "beat-to-beat" basis.

SUMMARY OF THE INVENTION

In accordance with this invention, a low level biological signal voltage from the body surface is amplified and displayed with greatly enhanced signal-to-noise ratio permitting continuous display of cyclical and non-cyclical events. This is accomplished by the use of plural sets of bipolar leads connected by electrodes to the body surface so as to obtain the same biological signal on each set of leads. The bipolar leads are connected, respectively, to plural low-noise biological amplifiers which provide simultaneous but separate amplification of the same signal. The amplified signals are added together in a summing circuit with the effect of noise reduction by averaging the random noise components and by reinforcement of the signal.

According to the invention, a plurality of sets of bipolar leads are used for deriving the same signal voltage from each of several closely spaced locations. Each set of bipolar leads is connected with the input of a high gain amplifier for separately amplifying the signal voltage from the respective leads. The outputs of the plural amplifiers are connected with a summing circuit for averaging the noise components. A display means is coupled with the output of the summing circuit for graphically displaying the time variation of the signal voltage. Further, noise composed of synphasic components is suppressed by negative feedback between the active electrodes and the reference electrode. Further, according to the invention, a low pass filter for passing the frequency range of the signal and rejecting noise above that frequency range is connected between the output of each of the amplifiers and the respective inputs of the summing circuit. For excluding noise components due to ambient electrical fields, especially of the supply mains frequency, a notch filter is coupled between the output of the summing circuit and the display means. Additionally, the system provides linear amplification up to a predetermined amplitude above which the amplification is non-linear with voltage clamping of high voltage components of the P wave and the QRS complex. The signal developed by any selected set of bipolar leads may be individually displayed by means of a channel selector switch and a final amplifier coupled between the low pass filters and the input of the display means.

A more complete understanding of this invention may be obtained from the detailed description that follows taken with the accompanying drawings.

BEST MODE FOR CARRYING OUT THE INVENTION

Figure 1:
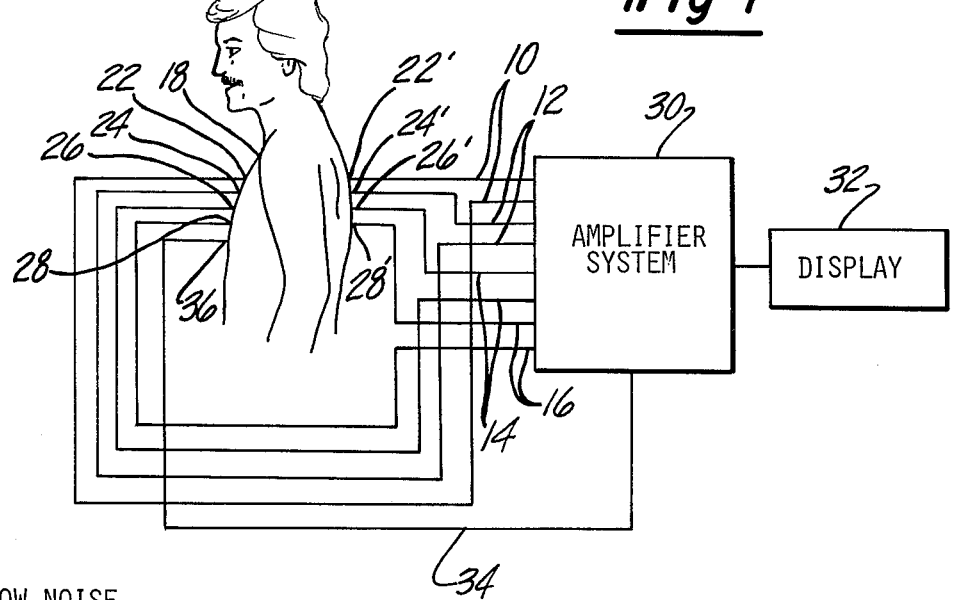
FIG. 1 is a diagram showing the amplifier system with a bipolar lead connection to a patient.

Referring now to the drawings, there is shown an illustrative embodiment of the invention in a system for detection of the cardiac conduction system activity from the surface of the body on a beat-to-beat basis. It will be appreciated as the description proceeds, that the invention may be useful in other applications.

FIG. 1 shows a system, in generalized form, incorporating the subject invention as applied to a patient. It comprises plural sets of active bipolar leads 10, 12, 14 and 16 which are connected to the body 18 of the patient. In particular, one of the bipolar leads 10 is connected by an electrode 22 to the chest region and the other is connected by an electrode 22' to the back region. Similarly, the bipolar leads 12 are connected by electrodes 24 and 24' to the chest and back regions respectively, the bipolar leads 14 are connected by electrodes 26 and 26' to the chest and back regions respectively, and the bipolar leads 16 are connected by electrodes 28 and 28' to the chest and back regions respectively. The electrodes 22, 24, 26 and 28 may be considered to be positive electrodes and are attached to the body at closely spaced locations while the electrodes 22', 24',26' and 28' constitute negative electrodes and are attached to the body at closely spaced locations. Thus, all of the sets of bipolar leads sense the same biological signal voltage from the body surface.

The bipolar leads 10, 12, 14 and 16 are connected as inputs to the amplifier system 30 of this invention. The output of the amplifier system is applied to a display means 32 which may take the form of either a cathode ray oscilloscope or a strip chart recorder of the type commonly used with the conventional electrocardiograph. The amplifier system 30 applies a negative feedback signal on a lead 34 to a reference electrode 36 for purposes to be described subsequently. The amplifier system 30 will be described in detail subsequently.

Figure 2:
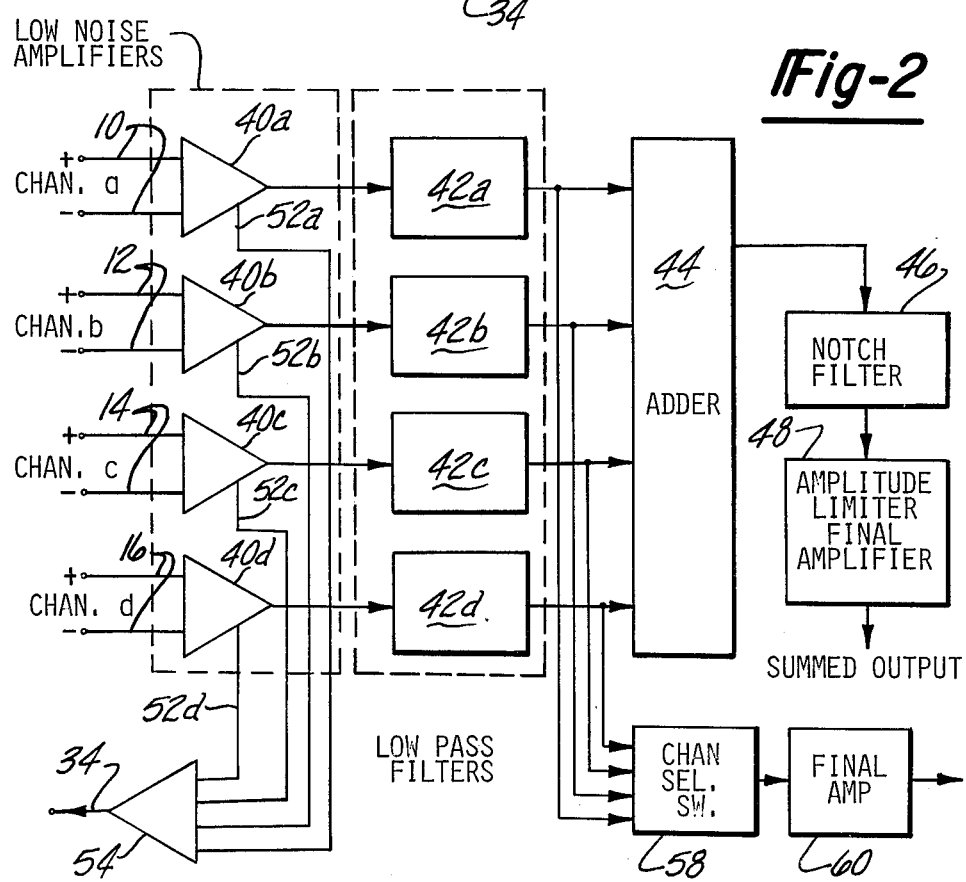
FIG. 2 is a block diagram of the amplifier system incorporating the invention.

FIG. 2 is a block diagram of the amplifier system 30. The system comprises a plurality of parallel input channels a, b, c and d including, respectively, low noise amplifiers 40a, 40b, 40c and 40d having inputs connected, respectively, with the sets of bipolar leads 10, 12, 14 and 16. In the illustrative embodiment, there are four sets of active leads and amplifier channels; it will be appreciated that, in the general case, there may be "n" channels where "n" is any whole number, depending upon the results desired. Each amplifier, for example, exhibits a gain of 1,000 over the bandwidth of 25 to 1,000 hertz.

In order to eliminate noise voltage components in the frequency range above the signal frequency, the output of each amplifier is suitably filtered. For this purpose, a plurality of low pass filters 42a, 42b, 42c and 42d are connected, respectively, with the outputs of the amplifiers 40a, 40b, 40c and 40d. In the illustrative embodiment, each of the low pass filters has a cutoff frequency of 300 hertz and exhibits an attenuation of 20 db per octave.

The amplified and filtered signals with attendant noise are additively combined in order to improve the signal-to-noise ratio. For this purpose, the output of each of the low pass filters 42a, 42b, 42c and 42d are connected with an input of a summing circuit 44. In the summing circuit, the signals are combined additively so that the random noise attendant with the signal is combined additively with the effect of substantial cancellation so that the noise level is reduced and the signal-to-noise ratio is greatly increased.

The output of the summing circuit 44 may include noise components derived from ambient electrical fields. In particular, a component corresponding to the 60 hertz frequency of the supply mains is most likely to be introduced in each of the amplifier channels in an in-phase relationship. To reject this noise component, a notch filter 46 has its input connected with the output of the summing circuit 44. The notch filter provides a large attenuation at the frequency of the supply mains or other selected frequencies, as desired.

The output of the notch filter 46 is applied to the input of a final amplifier and limiter 48. The amplifier and limiter provides linear amplification up to a predetermined amplitude, for example, 50 millivolts and, above this level the amplification is non-linear with voltage clamping of the high voltage components of the P wave and the QRS complex. The output of the final amplifier and limiter 48 is applied to the input of the display, either a cathode ray oscilloscope or a strip chart recorder.

In the system as described above, with the summing of plural channel signals, certain noise components such as muscle activity noise and supply mains interference, are introduced to all channels synchronously and to a similar degree. Such noise components, sometimes called symphasic components, require a high degree of suppression because of their tendency to reinforce each other in the summing circuit. This suppression is provided by the use of a current source technique in each amplifier, which will be described subsequently, and by negative feedback between the active electrodes and the reference electrodes. In order to provide the negative feedback, each of the amplifiers 40a, 40b, 40c and 40d have secondary outputs 52a, 52b, 52c and 52d, respectively, which are connected to the respective inputs of a feedback amplifier 54. The output of the feedback amplifier 54 is applied to the reference electrode 36 through the lead 34. The negative feedback applies the amplified noise components with inverted polarity to the body of the patient so that there is a cancellation of the corresponding components between the active electrodes and the reference electrode.

In order to permit independent display of the output of any channel, a channel selector switch 58 and a final amplifier 60 are provided for selectively coupling the output of the filters 42a, 42b, 42c and 42d to the input of the display 32. For this purpose, the output of each filter is connected with a respective input of the channel selector switch 58 and the output of the switch is connected to the input of the final amplifier 60. The output of the amplifier 60 is applied to the input of the display 32.

Figure 3:
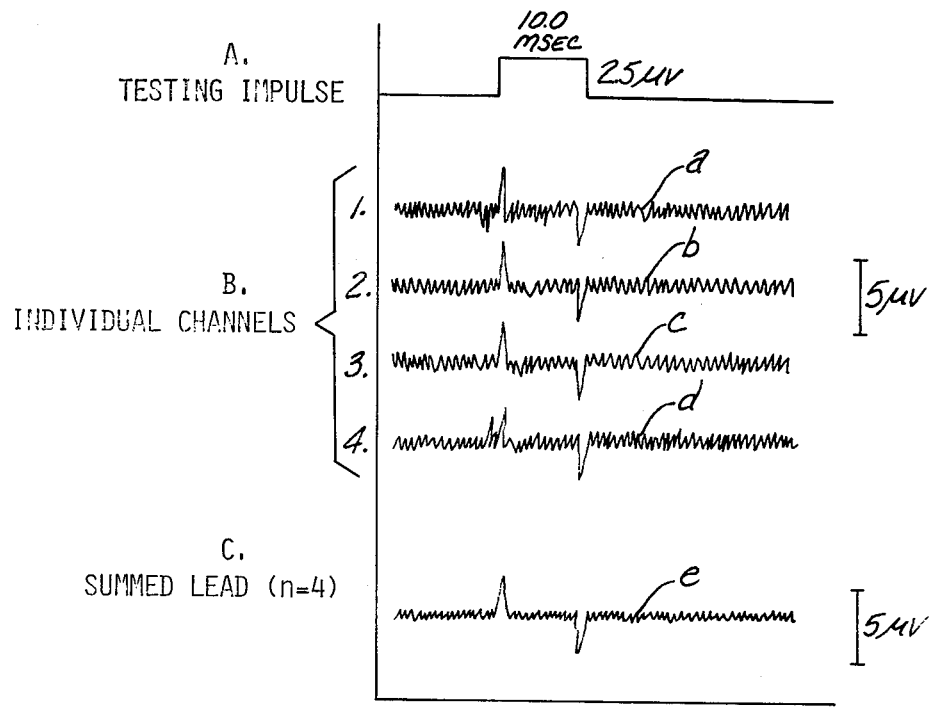
FIG. 3 is a diagram of waveforms produced by a calibration pulse.

The improvement in signal-to-noise ratio of the amplifier system is illustrated by operation with a calibration signal input, as represented by the waveforms of FIG. 3. The calibration signal is applied to each of the inputs of the respective amplifiers 40a, 40b, 40c and 40d. This input signal is a square wave pulse A having an amplitude of 2.5 microvolts and a duration of 100 milliseconds. The output signals of the individual channels, taken at the outputs of the low pass filters 42a, 42b, 42c and 42d, are represented by the waveforms a, b, c and d, respectively. In each of these waveforms the positive voltage spike represents the leading edge of the calibration pulse A and the negative voltage spike represents the trailing edge. The low level amplitude variations in each waveform represent random noise and a 60 hertz interference from the supply mains. The noise amplitude at the output of each individual channel is about 1 microvolt. The summation of the channel output voltages is represented by the waveform e. In this waveform, the low level amplitude variations represent the summation of the random noise components and the 60 hertz components. The random noise amplitude in the output of the summing circuit, as illustrated by waveform e, is less than one-half of that in the individual channels.

Figures 4A, 4B:
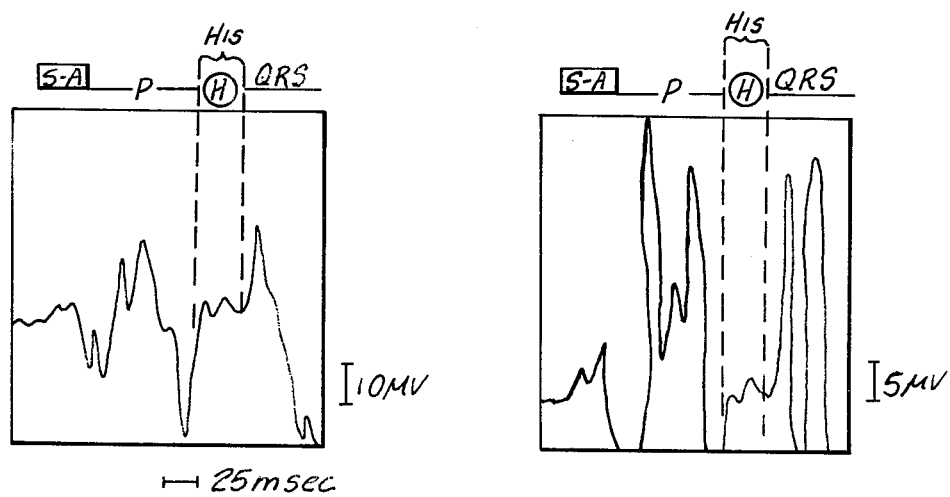
FIG. 4a is a recording of a single beat according to the invention.
FIG. 4b is a recording obtained by the signal averaging technique.

FIGS. 4a and 4b are different waveform recordings of the cardiac conduction system activity of the same patient. FIG. 4a represents a single beat recording according to this invention. FIG. 4b represents a recording obtained by signal averaging of 256 consecutive cardiac cycles. The early pre-P (sinus node region) activity deflections are very similar and the His bundle activity deflections are nearly identical. The difference in the P wave and the QRS activity deflections are due primarily to the voltage clamping in the single beat recording and to the filter effect in the averaged recording. Both recordings were obtained in the same subject with the same time base and trigger lead and similar location of the electrodes forming an antero-posterior (Z) bipolar transthoracic lead. Single Z lead was used for the averaged recording. Single beat recording was obtained from summing the four parallel anteroposterior bipolar transthoracic leads ($Z_2$–$Z_5$). The electrodes were placed in a vertical arrangement anteriorly in the second ($Z_2$), third ($Z_3$), fourth ($Z_4$) and fifth ($Z_5$) intercostal space parasternally and in the corresponding left paraspinal locations posteriorly.

Figure 5A:
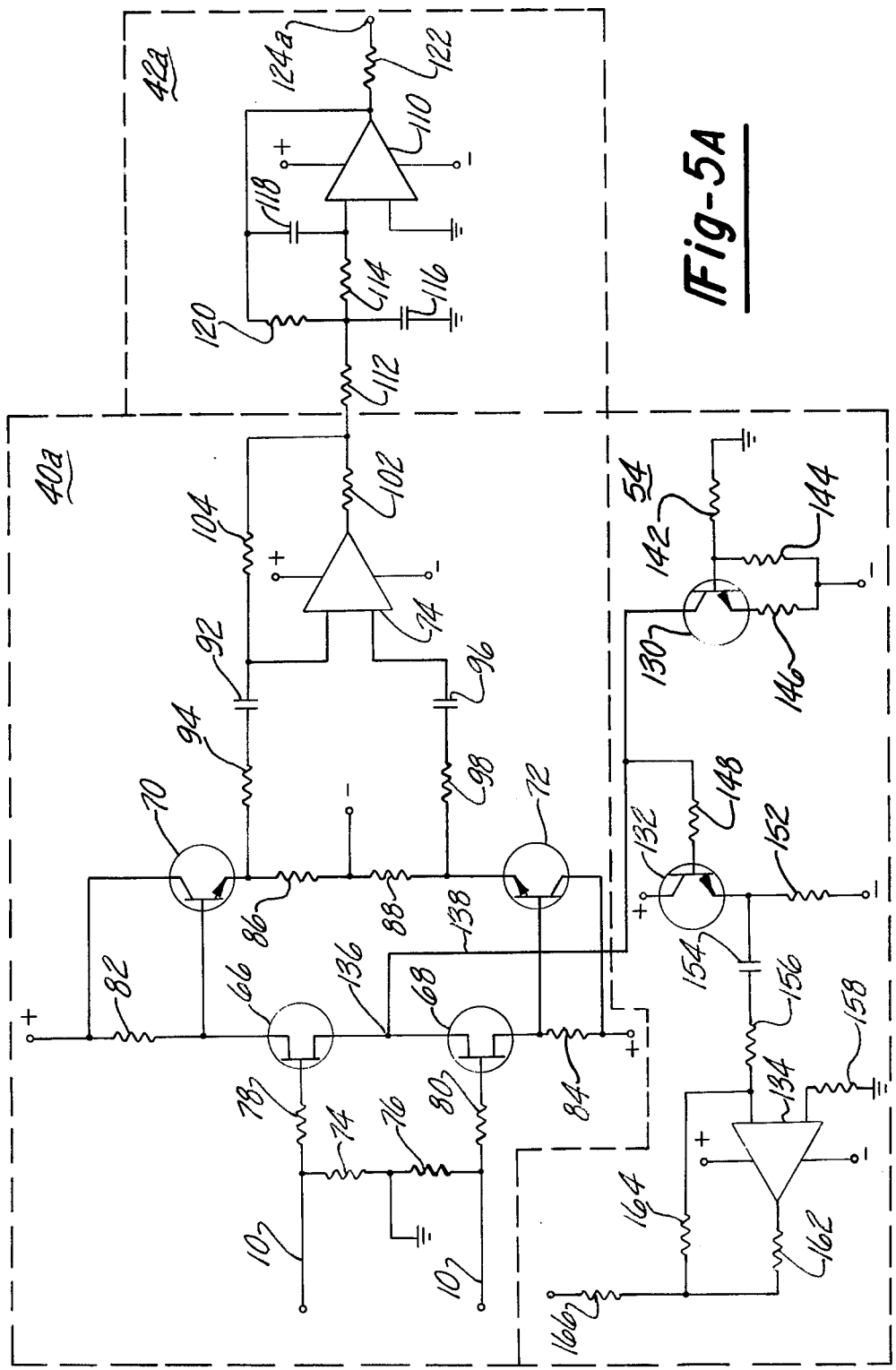
FIGS. 5a and 5b are schematic diagrams of the amplifier system incorporating this invention.
Figure 5B:
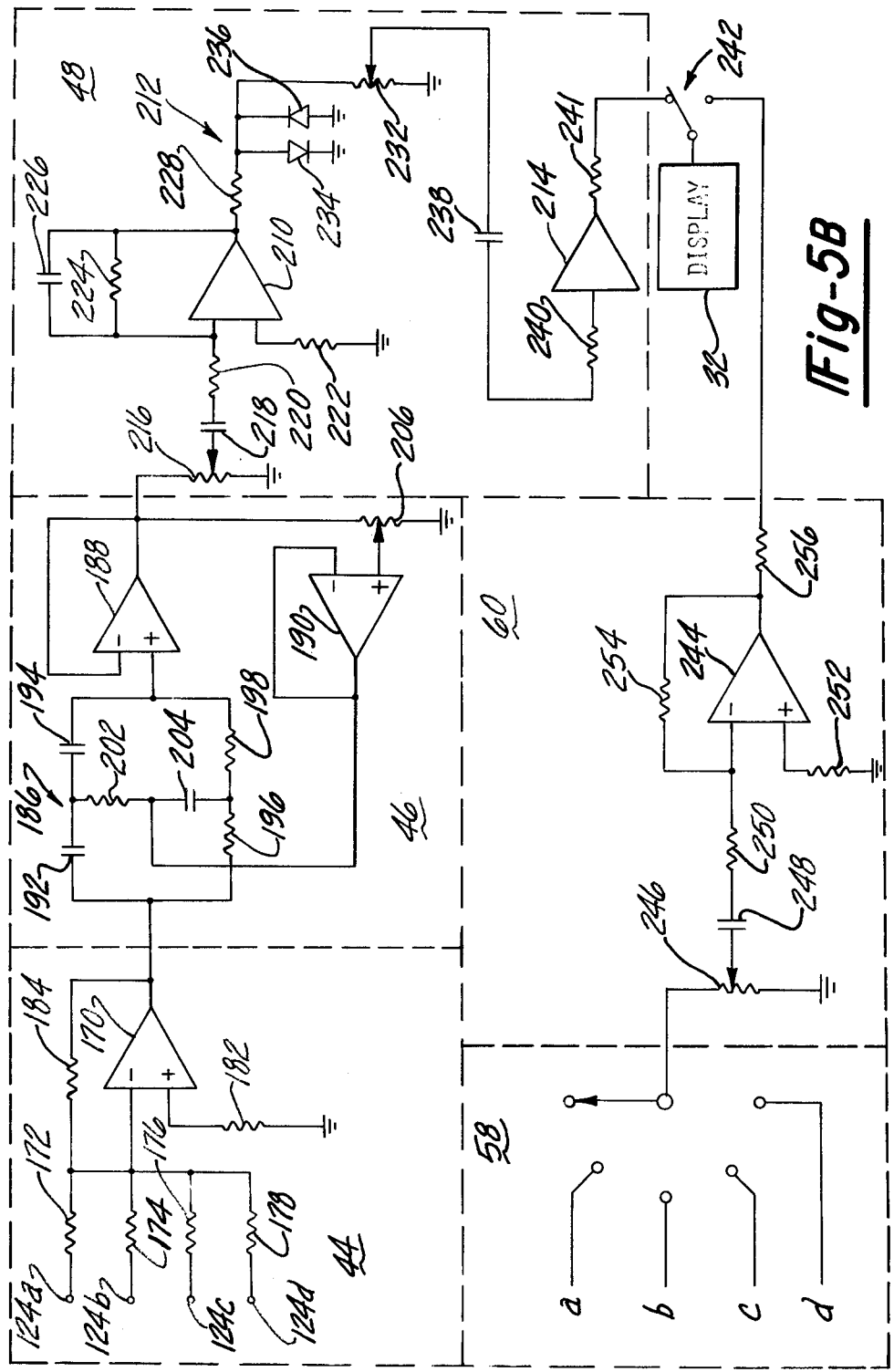

The amplifier system of this invention is shown in schematic diagram in FIGS. 5a and 5b. The schematic diagram of FIG. 5a shows only one of the amplifier channels, namely amplifier 40a and low pass filter 42a, it being understood that the other amplifier channels are identical.

The amplifier 40a is a differential amplifier comprising, in general, a field effect transistor (FET) 66 and a FET 68, a pair of bipolar transistors 70 and 72 and an operational amplifier 74. The FETs 66 and 68 constitute a voltage amplifier in which input leads 10 are connected across a pair of resistors 74 and 76 and through respective input resistors 78 and 80 to the respective gate electrodes of the FETs 66 and 68. The positive terminal of the power supply is connected through a resistor 82 to the source of FET 66 and through a resistor 84 to the source electrode of FET 68. The drain electrodes of FETs 66 and 68 are connected together.

The bipolar transistors 70 and 72 constitute a differential current amplifier coupled with the FET voltage amplifier. The transistor 70 has its base and collector electrodes connected across the resistor 82 and its emitter electrode is connected through a resistor 86 to the negative terminal of the power supply. Transistor 72 has its base and collector electrode connected across resistor 84 and its emitter electrode is connected through a resistor 88 to the negative terminal of the power supply.

The operational amplifier 74 has its non-inverting input coupled through a capacitor 92 and resistor 94 to the junction of resistor 86 and the emitter of transistor 70. The inverting input of the operational amplifier is coupled through a capacitor 96 and a resistor 98 to the junction of resistor 88 and the emitter of transistor 72. The output of the operational amplifier is coupled through an output resistor 102 and a feedback resistor 104 to the non-inverting input of the operational amplifier. The output of the operational amplifier is coupled through the output resistor 102 to the input of the low pass filter 42a.

The low pass filter 42a comprises a resistive-capacitive network and an operational amplifier 110. The resistive-capacitive network includes a pair of resistors 112 and 114 connected serially between the resistor 102 and the non-inverting input of the amplifier 110. A capacitor 116 is connected from the junction of resistors 112 and 114 to ground. A feedback capacitor 118 is connected between the output of the amplifier 110 and the non-inverting input and a feedback resistor 120 is connected between the amplifier output and the junction of resistors 112 and 114. The inverting input of the amplifier 110 is connected to ground. The output of the amplifier 110 is applied through an output resistor 122 to input 124a of the summing circuit 44.

The negative feedback amplifier 54 described above comprises, in general, bipolar transistors 130 and 132 and an operational amplifier 134. The input to the feedback amplifier is derived from the node 136 between the drain electrodes of the FETs 66 and 68. This node is connected through a conductor 138 to the collector of transistor 130. The base of the transistor is connected to the junction of resistors 142 and 144 which are serially connected between the negative terminal of the power supply and ground. The emitter of the transistor 130 is connected through a resistor 146 to the negative terminal of the power supply. The transistor 130 is coupled to the transistor 132 through a resistor 148 between the collector of transistor 130 and the base of transistor 132. The collector of transistor 132 is connected directly to the positive terminal of the power supply and the emitter is connected to the negative terminal through a resistor 152. The output of transistor 132 is coupled to the non-inverting input of the operational amplifier 134 by a capacitor 154 and a resistor 156. The inverting input of the amplifier is connected through a resistor 158 to ground. The output of the operational amplifier 134 is applied through an output resistor 162 and a feedback resistor 164 to the non-inverting input of the amplifier. The output is also applied through a resistor 166 to the reference electrode 36 on the patient.

As described above, each of the input channels of the amplifier system is the same as amplifier 40a and the low pass filter 42a, i.e. the amplifiers in all channels are matched and the low pass filters in all channels are matched. The outputs of the low pass filters are applied to the respective inputs of the summing circuit 44.

The summing circuit 44, notch filter 46 and amplitude limiter and final amplifier 48 are shown in the schematic diagram of FIG. 5b. The summing circuit 44 comprises an operational amplifier 170 and an input resistor network comprising summing resistors 172, 174, 176 and 178. Each of these resistors has one terminal connected to the inverting input of the amplifier 170; the other terminals of these resistors, namely 124a, 124b, 124c and 124d respectively, constitute the input terminals of the summing circuit. The non-inverting input of the amplifier 170 is connected through a resistor 182 to ground and a feedback resistor 184 is connected between the output of the amplifier and the inverting input thereof. The output of the amplifier 170 constitutes the output of the summing circuit and is coupled to the input of the notch filter 46.

The notch filter 46 comprises a resistance-capacitance network 186 and a pair of operational amplifiers 188 and 190. The network 186 comprises a pair of capacitors 192 and 194 connected in series between the output of the summing circuit 44 and the non-inverting input of the operational amplifier 188. It also comprises a pair of series resistors 196 and 198 connected in series between the output of the summing circuit and the non-inverting input of the amplifier 188. Additionally, the network includes a resistor 202 and a capacitor 204 connected in series between the junction of capacitors 192 and 194 and the junction of resistors 196 and 198. The output of the operational amplifier 188 is fed back to its inverting input and it is also applied across a potentiometer 206. The movable contact of the potentiometer 206 is connected with the non-inverting input of the operational amplifier 190 which has its output fed back to the inverting input. The output of the amplifier 190 is also applied to the junction between the resistor 202 and the capacitor 204. The output of the notch filter 46 is taken across the potentiometer 206 and is applied to the amplitude limiter and final amplifier 48.

The limiter and final amplifier 48 comprises, in general, an operational amplifier 210, a limiter 212 and an operational amplifier 214. The output of the notch filter 46 is applied across a potentiometer 216 which has its movable contact connected through a capacitor 218 and series resistor 220 to the non-inverting input of the operational amplifier 210. The inverting input of the operational amplifier 210 is connected through a resistor 222 to ground. The output of the amplifier is fed back through parallel resistor 224 and capacitor 226 to the non-inverting input. The output of the amplifier is applied to the input of the limiter 212. The limiter 212 includes a resistor 228 and a potentiometer 232 connected in series between the output of the amplifier 210 and ground. A pair of voltage limiting diodes 234 and 236 are connected with opposite polarity in parallel across the potentiometer 232. The movable contact of the potentiometer 232 is connected through a series capacitor 238 and resistor 240 to the non-inverting input of the operational amplifier 214. The output of the amplifier 214 is connected through a resistor 241 to one fixed contact of a display selector switch 242. The movable contact of the selector switch 242 is connected to the input of the display 32. The individual channel outputs may also be applied to the display 32 through the selector switch 242, as will be described below.

The output of any one of the individual input channels a, b, c or d may be applied to the display 32 through the channel selector switch 58 and the amplifier 60. The channel selector switch 58 includes a set of fixed contacts 58a, 58b, 58c and 58d and a movable contact which is connected to the input of the variable gain amplifier 60. The amplifier 60 comprises an operational amplifier 244. The output of the selector switch 58 is applied across a potentiometer 246, the movable contact of which is connected through series capacitor 248 and resistor 250 to the inverting input of the amplifier 244. The non-inverting input of the amplifier is connected through a resistor 252 to ground. The output of the amplifier is applied through a feedback resistor 254 to the inverting input. The output of the amplifier 244 is applied through an output resistor 256 to the other fixed contact of the display selector switch 242.

With the display selector switch 242 closed against the lower contact, the output channel a, b, c or d may be displayed on display 32 according to the setting of channel selector switch 58. With the display selector switch closed against the upper contact, the output of the summing circuit 44, as modified by notch filter 46 and the limiter and final amplifier 48, is displayed on the display 32.

Although the description of this invention has been given with reference to a particular embodiment, it is not to be construed in a limiting sense. Many variations and modifications will now occur to those skilled in the art. For a definition of the invention, reference is made to the appended claims.

What is claimed is:

1. An amplifier system for displaying a biological signal voltage from a body surface, comprising:
    a plurality of sets of bipolar leads with one lead of each set coupled to the body surface at a first set of closely spaced locations all of which produce the same signal voltage and with the other lead of each set coupled to the body surface at a second set of closely spaced locations all of which produce the same signal voltage,
    a plurality of amplifiers each having its input coupled with a different one of said sets of leads for amplifying said signal voltage,
    a summing circuit having a plurality of inputs each being coupled with the output of a different one of said amplifiers for adding the amplified signal voltages,
    and display means coupled with the output of the summing circuit for graphically displaying the time variation of said signal voltage.

2. The invention as defined in claim 1 including a low pass filter connected between the output of each of said amplifiers and the respective input of said summing circuit.

3. The invention as defined in claim 2 including a notch filter coupled between the output of said summing circuit and said display means.

4. The invention as defined in claim 3 including a voltage limiter and amplifier coupled between said notch filter and said display means.

5. The invention as defined in claim 1 including a reference electrode adapted to be connected to said body,
    an inverting summing circuit having a plurality of inputs coupled respectively with the outputs of said amplifiers,
    the output of said inverting summing circuit being coupled with said reference electrode.

6. The invention as defined in claim 4 including a channel selector switch having a plurality of inputs each being connected with the output of one of said low pass filters,
    a final amplifier having an input coupled with the output of the channel selector switch,
    and means for selectively coupling said display means with the output of said final amplifier.

7. An amplifier system for displaying a biological signal voltage from a body surface, comprising:
    a plurality of leads coupled to the body surface at closely spaced locations, all of which produce the same signal voltage,
    a plurality of amplifiers each having its input coupled with a different one of said leads for amplifying said signal voltage,
    a summing circuit having a plurality of inputs each being coupled with the output of a different one of said amplifier for adding the amplified signal voltages,
    and display means coupled with the output of the summing circuit for graphically displaying the time variation of said signal voltage.

* * * * *